United States Patent
Renfroe et al.

(12)

(10) Patent No.: US 7,473,429 B1
(45) Date of Patent: Jan. 6, 2009

(54) METHOD FOR TREATMENT OF LAMINITIS IN ANIMALS

(76) Inventors: J. Ben Renfroe, 224 Northcliffe Dr., Gulf Breeze, FL (US) 32561; Daniel W. Carter, 1301 Soundview Trail, Gulf Breeze, FL (US) 32561

( * ) Notice: Subject to any disclaimer, the term of this patent is extended or adjusted under 35 U.S.C. 154(b) by 12 days.

(21) Appl. No.: 11/881,607

(22) Filed: Jul. 27, 2007

(51) Int. Cl.
*A61K 39/08* (2006.01)
*A61K 31/715* (2006.01)

(52) U.S. Cl. .................... 424/247.1; 514/54; 424/236.1

(58) Field of Classification Search ........................ None
See application file for complete search history.

(56) References Cited

U.S. PATENT DOCUMENTS

| | | | | |
|---|---|---|---|---|
| 5,562,907 A | * | 10/1996 | Arnon | 424/236.1 |
| 2002/0064536 A1 | * | 5/2002 | Hunt | 424/247.1 |
| 2003/0138460 A1 | * | 7/2003 | Hunt | 424/239.1 |
| 2004/0013687 A1 | * | 1/2004 | Simpson et al. | 424/190.1 |
| 2005/0238667 A1 | * | 10/2005 | Hunt | 424/239.1 |
| 2008/0003241 A1 | * | 1/2008 | Marx et al. | 424/239.1 |

OTHER PUBLICATIONS

Bohnel, H et al, J. Vet. Med., vol. 48, pp. 373-383, 2001, Visceral botulism-A New form of Bovine Clostridium botulinum Toxication.*
'Grass Sickness and some thoughts on its prevention', found on Google under Equine Grass Sickness and herefordequestrian medical conditions, made available on line Mar. 13, 2006.*

* cited by examiner

*Primary Examiner*—Mark Navarro
*Assistant Examiner*—Ginny Portner
(74) *Attorney, Agent, or Firm*—William H. Hollimon

(57) ABSTRACT

The present invention generally relates to methods for treating the sequela of laminitis in hoofed animals. Benefits are obtained by administering to the animals to be treated injections of Botulinum Toxin in the limb to be treated. In one embodiment, about 100 Units to 600 Units of Type A Botulinum Toxin is injected in multiple injections into the flexor digitorum profundus muscle of an animal's affected limb.

9 Claims, No Drawings

METHOD FOR TREATMENT OF LAMINITIS IN ANIMALS

BACKGROUND OF THE INVENTION

1. Field of the Invention

This invention relates to laminitis in animals. More specifically, the invention comprises a method of treating the sequela of laminitis in animals, particularly horses.

2. Description of the Related Art

Laminitis is a serious medical condition in horses and other hoofed animals, and despite significant advances in veterinarian medicine, remains a major reason for euthanasia of such animals. Laminitis is an inflammation of the lamina (the lamellar attachment between the distal phalanx (coffin bone) and the inner hoof wall. Laminitis is characterized by separation of the hoof wall from the distal phalanx due to the deterioration and detachment of the lamina, which holds the two together. Failure of the laminar attachments, in a majority of cases is limited to the toe region (commonly called rotation). It is hypothesized that without the distal phalanx properly attached to the inside of the hoof wall, the weight of the horse and the forces of locomotion by the deep digital flexor tendon cause the distal phalanx to rotate away from the hoof capsule. This process shears the vasculature and crushes the corium (dermis) of the sole, causing unrelenting pain and a characteristic lameness. Radiographic and necropsy examination of the feet of affected horses show a characteristic rotation of the dorsal border of the distal phalanx away from the dorsum of the hoof wall.

In more rare and significantly more severe cases the failure of attachment can extend around the perimeter of the hoof. This allows the entire bony column to drop within the hoof capsule.

Laminitis can occur secondary to many diseases of the horse, but is common following overeating, colic, fever, shock, pneumonia, injury and obesity.

All hoofed animals, and particularly horses, are susceptible to laminitis and significant economic loss occurs due to severe pain and debilitation of these animals. Due to the insidious nature of the disease process, damage to the laminae often occurs prior to clinical evidence of abnormality.

There is no cure for laminitis. Current medical therapies include identification and treatment of the underlying disease, systemic anti-inflammatory medications and rest. A more aggressive treatment of the sequela of laminitis involves severing the deep digital flexor tendon. Additionally, support of the sole has met with some success utilizing deep sand flooring, peat moss and foam sole pads.

One example of treatment is the application of wedge shoes. Elevation of the heels with wedge shoes reduces the pull of the deep digital flexor tendon on the coffin bone and therefore decreases the stress on the dorsal laminar attachment. However, there are several disadvantages to the wedge shoe therapy. First, the wedge shoe creates additional stresses on other regions of the foot and may cause compression of the hoof capsule during the acute phase. The second disadvantage to wedge shoes involves the method of attaching the wedge shoe to the hoof. If wedge shoes are nailed onto the hoof, the hoof capsule may be compressed, due to the nailing force, potentially leading to further damage. If wedge shoes are glued onto the hoof the horse may be forced to hold one foot up for an extended period of time thereby harming the opposite foot. To reduce risk of further damage it is recommended that wedge shoes are bandaged to the foot during the acute phase. However, if the bandaged shoe slips from the hoof it could cause an abrupt strain on the deep digital flexor tendon and potential further damage to the dorsal laminar attachment. Another disadvantage to wedge shoes is the risk of increased damage if the angle of the wedge does not correspond to each horse's particular condition. Wedge shoes must be designed for each horse on a case by case basis based on the severity of the condition or based on the hoof's adaptation to the condition before any treatment was given. In order to properly treat the condition different horses may require the wedge shoes to be adjusted to different angles. If the angle of the wedge is improper the condition may become more severe.

Surgical transection of the deep digital flexor tendon (DDFT) has also been used to reduce the shearing forces during the acute phase of laminitis. One study reported a 60% survival rate at 2 years after the procedure. Those animals who do recover from the severing of the deep digital flexor tendon are usually not comfortable enough to ride. Even with these issues in mind, current veterinary practices suggest that a deep digital flexor tenotomy is the fastest way to counteract the rotational forces and restore the perfusion and tissue mass to the dorsal regions of the foot.

Accordingly, there is a need for a proactive treatment that effectively treats and/or prevents the laminitis and its sequela. This treatment would effectively treat these conditions without requiring invasive surgery and all the risks and side effects associated with such invasive surgery.

BRIEF SUMMARY OF THE INVENTION

The present invention comprises a method for treatment and/or prevention of the sequela of laminitis in animals. More specifically, the present invention comprises a method for treatment of the symptoms associated with the laminitis syndrome.

Laminitis is the condition in which the lamina becomes inflamed. This inflammation may lead to separation of the epidermal lamina from the dermal lamina associated with the distal phalanx (coffin bone) often resulting in the rotation or sinking of the distal phalanx within the hoof capsule. In the acute stage the lamina are inflamed but the distal phalanx is not yet displaced. Upon entering the chronic phase of the laminitis condition the distal phalanx may be displaced. Some horses compensate for the displacement by stabilizing the bone in its displaced position.

The rotation of this distal phalanx (coffin bone) may be due to a metabolic disturbance (such as carbohydrate load) or to a discrepancy between the strength of the epidermal laminae and the load they have to support. The forces of the deep digital flexor tendon on the palmar aspect of the digital phalanx are thought to contribute to the tearing of the laminar membrane in the toe region. To ease the tension of the deep digital flexor tendon, thereby reducing the pull on the distal phalanx and preventing further laminar tearing or displacement of the distal phalanx the method of the present invention can be implemented.

The pull of the deep digital flexor tendon on the coffin bone is thought to affect the foot in several different ways. First, the tightening may compromise the blood flow through the dorsal lamina. The decrease in blood flow may cause decreased laminar perfusion. With a decrease in laminar perfusion lamina tissue is deprived of nutrients and is weakened and more subject to tearing. Second, the tightening of the deep digital flexor tendon on the palmar aspect of the digital phalanx creates a force which pulls the laminar membrane away from the digital phalanx or hoof wall. The pull of the deep digital flexor tendon on the distal phalanx often causes the distal phalanx to become displaced as the opposing force of the laminar attachment is impaired.

Because mechanical failure of the dorsal lamina may result in separation of the distal phalanx from the hoof wall, the method of treatment of the present invention may be directed at relieving the tensile forces acting on the bone, which contribute to this separation. Reducing the pull of the deep digital flexor tendon on the palmar aspect of the distal phalanx theoretically reduces the shear forces on the lamina which attaches the dorsal surface of the distal phalanx to the hoof wall. The relaxation of the deep digital flexor tendon may preserve laminar perfusion. If the tensile forces acting on the distal phalanx are relieved, in the acute stage of the condition, it may prevent the distal phalanx from displacing and entering the chronic phase. If the displacement of the distal phalanx can be prevented a horse has a good chance of recovery. Where a horse has entered the chronic phase the distal phalanx is displaced downward and compresses the sole corium altering the architectural development of the hoof capsule. It is hypothesized that by relaxing the deep digital flexor tendon the distal phalanx will re-align with relation to the ground surface and the hoof capsule can begin to regenerate itself. The goal is to allow the hoof to reestablish normal orientation of the distal phalanx and maintain that orientation without the aid of the clinical relaxation of the deep digital flexor tendon that this treatment provides. Relieving the tensile forces acting on the distal phalanx is accomplished by injecting the flexor muscles of the animal with Botulinum Toxin Type A.

The Botulinum Toxin Type A used for treatment of the animal can be administered to the animal by any suitable method. For example, the Botulinum toxin type A can be injected into the muscle bellies of the flexor digitorum profundus muscle which attaches to the deep digital flexor tendon. Generally, the Botulinum toxin is administered in the amount of 100 U to 600 U over the course of 4 to 10 injections per muscle.

The above described treatment method can also be used to treat issues/pathologies distinct from laminitis. In some of these pathologies, treatment involves injections in the superficial and/or deep digital flexor muscle. These pathologies include "back in the knee" (deep and superficial); club foot in foals (deep and superficial); desmitis of the distal check ligament; navicular syndrome; trauma to the involved muscle or tendon; and inflammation of the involved muscle or tendon.

Laminitis can occur in any hoofed animal therefore the present invention should not be limited to horses.

DETAILED DESCRIPTION OF THE INVENTION

The following description contains significant detail regarding the novel aspects of the present invention. It should not be construed, however, as limiting the scope of the invention but rather as providing examples of the preferred method for treatment of the laminitis condition. Thus, the scope of the invention should be fixed by the following claims, rather than by the examples given.

The present invention is directed to the prevention and/or treatment of the sequela of the laminitis condition in animals. More specifically, the present invention is directed to a method for treating the symptoms of or aiding in the recovery of a hoofed animal afflicted with the condition commonly known as laminitis.

Generally, the method of treatment of the invention involves injecting Botulinum Toxin into the muscle bellies of the flexor digitorum profundus muscle. Botulinum Toxin, commonly known as BOTOX, MYOBLOC, OR DYSPORT, is a neurotoxic protein produced by the bacterium *Clostridium botulinum*. The toxin blocks the release of acetylcholine at the neuromuscular junction thereby relaxing the muscle. Typically, the physiologic effect of BOTOX lasts ten to twelve weeks.

Although much is still unknown about the laminitis condition most researchers agree that the pulling of the deep digital flexor tendon, attached to the palmar surface of the distal phalanx causes a shear force against the laminar membrane and altered blood flow to the laminar membrane. In severe cases that force may lead to the detachment or partial detachment of the lamina from the hoof wall. This detachment combined with the pull of the deep digital flexor tendon causes the distal phalanx to either rotate or sink in the hoof capsule. In severe cases the distal phalanx can protrude externally from the bottom of the hoof.

It is hypothesized that by reducing the pull of the deep digital flexor tendon on the palmar surface of the digital phalanx lamina damage will be reduced. In acute cases the relieving of the tensile forces on the deep digital flexor tendon could prevent the distal phalanx from displacing and entering a more severe phase of the laminitis condition. In the event that the hoof of the animal has already incurred lamina damage and bone displacement the reduced pull of the deep digital flexor tendon on the distal phalanx will allow the stabilization of bones within the hoof. Where the re-alignment of bones within the hoof takes place the hoof capsule can begin to regenerate and establish the restoration of sole tissue.

The inventor has discovered that administering Botulinum toxin type A is safe and effective for the treatment of the sequela of laminitis. Botulinum Toxin chemically denervates the muscle bellies effecting the tension of the deep digital flexor tendon. Due to the Botulinum Toxin the deep digital flexor tendon relaxes and reduces the force pulling on the palmar aspect of the distal phalanx. The disclosed treatment can be used for any laminitic animal.

There are seven serotypes of Botulinum Toxin (A through G). The present invention should not be limited to any one serotype of the toxin. In a preferred embodiment, for each limb to be treated, the Botulinum Toxin Type A is administered to the animal by injection into the muscle belly of the flexor digitorum profundus muscle at approximately 4 to 10 different sites in the muscle. The total amount of Botulinum Toxin Type A intramuscularly injected ranges from about 100 units to 600 units per limb depending on the size of the horse and the involvement of the affected muscles. Typically the Botulinum Toxin is administered after being reconstituted according to the manufacturer's recommendations at a desired dilution. In one example a quantity of 100 U of powdered BOTOX is dissolved in 2-4 cc's of preservative free, sterile saline. The region to be injected is prepped in a sterile fashion. The appropriate muscle is first identified anatomically, the muscle is then accessed utilizing an Ambu Neuroline Inoject 24 gauge, 2-3 inch coated needle electrode using EMG guidance. Botulinum Toxin is then injected through this needle into 4-6 sites in the involved deep digital flexor muscle belly.

Treatment should begin at the onset of any symptoms of laminitis. For prevention, treatment should begin in the contra-lateral limb as soon as an impaired weight bearing injury is evident. Some common symptoms include lameness, excess shifting of weight by the animal, altered heel stance, immobility, depression around the coronary band and increased frequency of animal lying down. If symptoms of laminitis do not improve the treatment should be repeated after two to six weeks. Treatment may also be repeated as needed if symptoms recur in the future.

Typically, an animal with laminitis in one limb will eventually show symptoms of laminitis in the contralateral uninvolved limb. Therefore even if an uninvolved limb shows no symptoms of laminitis the treatment may proceed in the uninvolved limb in an effort to prevent laminitis from occurring or progressing in the uninvolved limb.

The reader should note that although the above description and following examples relate to the treatment of laminitis in horses, it is believed that the method for treatment will work as described with any animal.

The present invention may be better understood with reference to the following examples.

EXAMPLE NO. 1

An 11 year old Tennessee Walking Horse with a history of laminitis was experiencing an acute exacerbation of the laminitis condition (Obel Grade 4). Botulinum toxin (Botox) was reconstituted into 100 units per 2 cc of normal saline. The skin overlying the flexor muscles of the fore legs was prepped with isopropyl alcohol. Using EMG guidance, 25 units of botulinum toxin was injected into 8 sites of the flexor digitorum profundus of each forelimb for a total of 400 units. The horse tolerated the procedure well with no immediate adverse effects noted. The horse was monitored over the next 12 weeks. Within 2 weeks the horse showed a marked improvement in it's ability to stand and ambulate. The horse has subsequently returned to functional use to the level of pasture comfort and occasional riding at all gaits.

EXAMPLE NO. 2

An eight year old stallion quarter horse was experiencing severe laminitis in two legs (Obel Grade 4). In leg 1 the deep digital flexor tendon was surgically cut utilizing accepted procedures and techniques. Redding shoes were applied at a 15 degree angle. In leg 2 utilizing clean technique and EMG guidance a total of 400 units of Botulinum Toxin Type A diluted into 8 cc of normal saline was injected into 8 separate sites within the flexor digitorum profundus. Redding shoes were applied at 15 degree angles. The horse underwent pre and post procedure venograms with no initial difference noted between the legs. The horse tolerated both procedures well and was monitored over the subsequent 5 weeks. The horse experienced a recovery from an Obel grade of 4 to an Obel grade of 3 with repeat venograms showing recovery of venous flow in both digits. Comparison between the two legs revealed a more rapid return to normal venous patterns in the limb receiving surgical transection of the deep digital flexor tendon. Thirty days post treatment the venogram of the surgical and Botulinum toxin treated legs were comparable.

EXAMPLE NUMBER 3

A 21 year old gelding quarter horse suffered a traumatic injury to the right fore carpus. Radiograph showed disruption of the normal arrangement of the carpal bones as well as severe swelling of the palmar aspect of the carpus. He was unable to extend the carpus in the non-weight bearing limb. This horse was diagnosed with traumatic disruption of the palmar ligaments of carpal bones including the accessory ligament of the deep digital flexor tendon. In an effort to prevent the development of laminitis in the contra-lateral limb, the horse received botulinum toxin 200 units (botox) injected into the deep digital flexor muscle as described above. The horse tolerated the procedure well. A Redden "Ultimate" shoe was also placed. The horse was monitored over the next 7 months. At one week and again at one month examination found no clinical evidence of laminitis in the left fore-limb. At two months the therapeutic shoe was removed. The horse was "toe touching" with the injured (right) fore-limb. At seven months the horse shows no evidence of laminitis in the left fore-foot (clinically or radiographically). The horse is now pasture sound.

EXAMPLE 4

A 23 year old female Tennessee Walking horse had chronic laminitis with rotation exceeding 20 degrees radiographically in all four feet (Obel Grade 4, recumbent). She exhibited a body condition score of 7 (significantly overweight). Examination revealed pressure sores on hips. The horse was shod with a reverse keg shoe. The dorsal aspect of hoof was shaved in the bilateral front feet to reduce the angle of deviation between dorsal aspect of coffin bone and the dorsal hoof wall. Utilizing the method described above the horse was injected with 200 u into the deep digital flexor muscle of each fore-limb. The horse tolerated the procedure well and experienced no adverse effects throughout the eight months of follow-up.

At ten days post injection the horse had improved to an Obel grade 3. At six weeks post injection the horse had improved to an Obel grade of 2. At five months post injection the horse was an Obel grade 1. Radiographically the coffin bone is parallel to the hoof wall. She is pasture sound.

EXAMPLE 5

A 12 year old Arabian gelding with a body condition score of six presented with a mis-diagnosed navicular syndrome, sequestrum of dorsal aspect of P3. He had undergone an operative procedure for this diagnosis. The horse was subsequently taken to a tertiary equine center and diagnosed with bilateral fore-limb laminitis. There the horse was treated conservatively with NSAIDs and Redden "ultimate shoes" on both forelimbs as well as stall confinement. The horse was referred to our center for ongoing care and follow-up locally.

On examination locally the horse exhibited an Obel Grade 3, almost 4. On observing the gait the horse appeared more painful in right fore-limb. X-ray of the limbs at that point indicated increased rotation by 12 degrees since discharge from the tertiary care center. Due to the asymmetry the horse initially underwent injection of the right fore-limb with 200 units of botulinum toxin A (Botox) in the deep digital flexor muscle utilizing the aforementioned technique.

19 days after the initial injection the horse was noted to have comparably increased pain in the left (uninjected) fore-limb. The right forelimb exhibited an Obel grade of 2 turning to the right. Turning to the left the horse exhibited an Obel grade of 3. It was therefore decided to proceed with injection of the left fore-limb. The horse received 200 units of botulinum toxin A (Botox) into the deep digital flexor muscle of the left fore-limb.

At 33 days post initial injection the horse was comfortable, exhibiting an Obel grade of 1 bilaterally.

What is claimed is:

1. A method for treating the sequela of a laminitis condition in an affected limb of a horse comprising:
   injecting a Botulinum Toxin, in a therapeutically effective amount sufficient to treat said laminitis condition into a flexor digitorum profundus muscle of said affected limb, said therepatically effective amount insufficient to cause death or paralysis of said horse when injected as such.

2. A method as defined in claim 1, wherein said Botulinum Toxin comprises Botulinum Toxin Type A.

3. A method as defined in claim 1, wherein said Botulinum toxin is administered to said animal in an amount from about 100 Units to 600 Units.

4. A method as defined in claim 1, wherein said Botulinum Toxin is injected into said flexor digitorum profundus muscle in four to ten injections.

5. A method for preventing laminar detachment in a limb of a horse having the sequela of a laminitis condition in said limb comprising:

injecting a Botulinum Toxin, in a therapeutically effective amount sufficient to prevent laminar detachment into a flexor digitorum profundus muscle of said limb, said therepatically effective amount insufficient to cause death or paralysis of said horse when injected as such.

6. A method as defined in claim 5, wherein said Botulinum Toxin comprises Botulinum Toxin Type A.

7. A method as defined in claim 5, wherein said Botulinum Toxin is administered to said animal in an amount from about 100 Units to 600 Units.

8. A method as defined in claim 5, wherein said Botulinum Toxin is injected into said flexor digitorum profundus muscle in four to ten injections.

9. A method for treating the sequela of a laminitis condition in an affected limb of a hooved animal comprising: administering a plurality of injections of Botulinum Toxin Type A, each of said injections containing a pharmaceutically effective amount of Botulinum Toxin Type A, into the flexor digitorum profundus muscle of said affected limb, of said hooved animal.

\* \* \* \* \*